United States Patent
Kovalsky et al.

[11] Patent Number: 5,998,789
[45] Date of Patent: Dec. 7, 1999

[54] CONVERTING ULTRAVIOLET LIGHT TO VISIBLE LIGHT WITH FLUORESCENT DYED POLYMER FOR PHOTOGRAPHY AND ANALYSIS OF ELECTROPHORESIS GELS

[76] Inventors: Alvin Kovalsky; Max D. Miller, both of 6421 E. Alondra Blvd., Paramount, Calif. 90723-3759

[21] Appl. No.: 09/063,621

[22] Filed: Apr. 20, 1998

Related U.S. Application Data

[60] Provisional application No. 60/045,020, Apr. 28, 1997.
[51] Int. Cl.$^6$ ................................................... H05B 35/00
[52] U.S. Cl. .................. 250/302; 250/504 R; 250/505.1
[58] Field of Search ..................................... 250/302, 303, 250/505.1, 504 R; 362/230, 231

[56] References Cited

U.S. PATENT DOCUMENTS 5,736,744   4/1998   Johannsen et al. ................. 250/504 R

*Primary Examiner*—Kiet T. Nguyen

[57] ABSTRACT

A fluorescent dyed polymer sheet receives excitation energy from ultraviolet wavelengths from 200 nanometers to 370 nanometers and converts to visible light wavelengths. This conversion allows for use of existing ultraviolet light sources to produce visible light for visualizing, photographing, documenting and analyzing electrophoresis gels produced with visible stains. An ultraviolet transilluminator is designed to fluoresce Ethidium bromide stained gels when exposed to ultraviolet light. This process allows visualization of the DNA and RNA bands providing images that can be photographed with black and white photographic cameras or video cameras. By placing the proper fluorescent dyed polymer on the surface of the ultraviolet transilluminator the polymer sheet receives excitation energy from the ultraviolet bandwidth and converts it to visible light wavelength emissions.

13 Claims, 3 Drawing Sheets

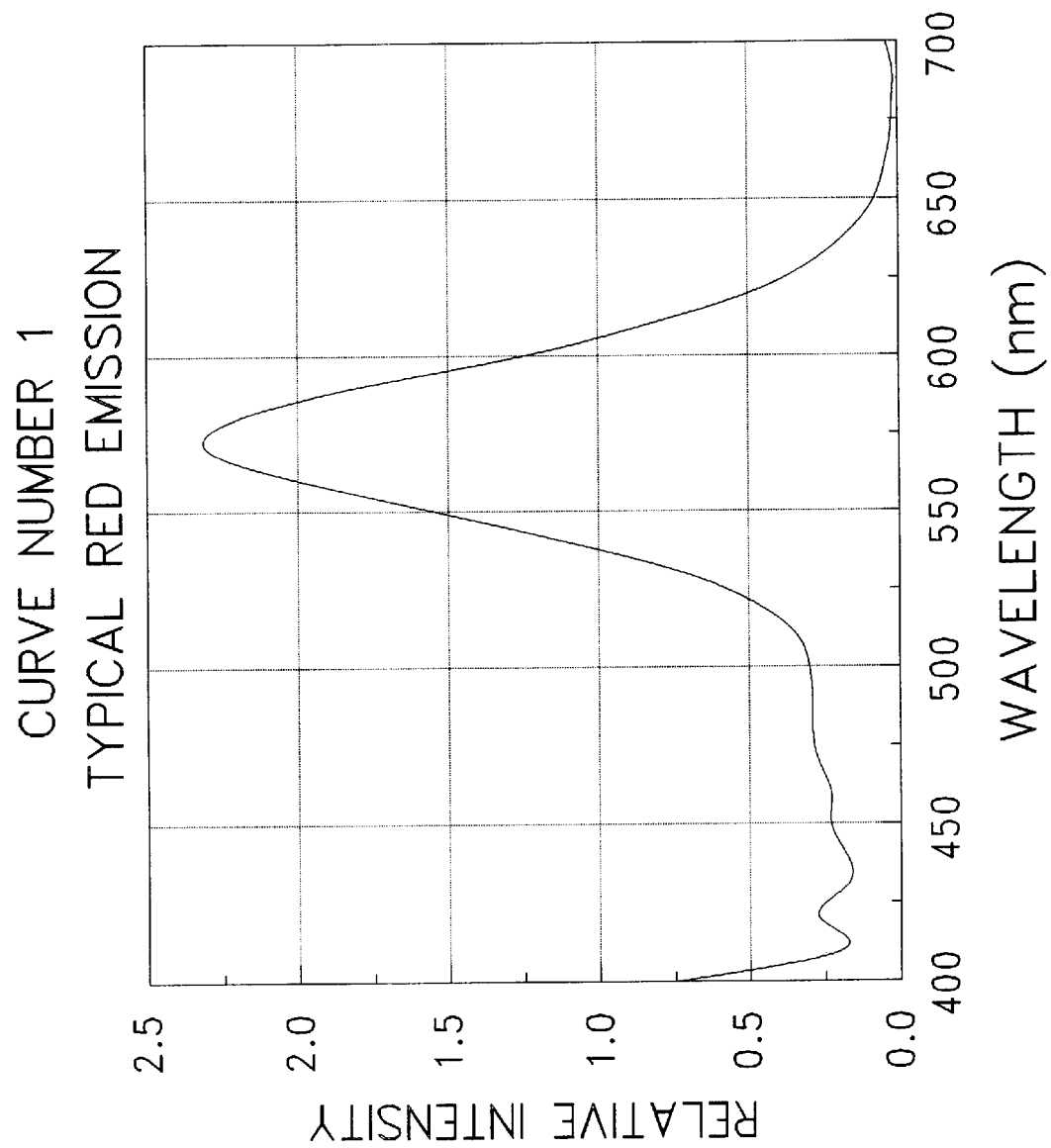

CONVERTING ULTRAVIOLET LIGHT TO VISIBLE LIGHT WITH FLUORESCENT DYED POLYMER FOR PHOTOGRAPHY AND ANALYSIS OF ELECTROPHORESIS GELS

This application claims priority from Provisional Application number 60/045,020, filed Apr. 28, 1997.

BACKGROUND OF INVENTION

1. Field of the Invention

The present invention relates generally to the field of Electrophoresis process involving the visualization, documentation and analysis of DNA and RNA gels. The invention specifically involves the photographic process and the analysis capability of the process.

2. Description of the Prior Art

Agarose Gel of DNA

The standard method used to separate, identify, and purify DNA fragments is electrophoresis though agarose gels. This technique is rapid, simple and is able to resolve mixtures of DNA fragments that can not be resolved with other methods. Moreover, the location of the DNA within the gel can be directly determined. DNA bands are stained with ethidium bromide for visualization. Ethidium bromide is a fluorescent dye substance containing a planar group able to intercalate between the stacked bases of the DNA. UV-irradiation absorbed by the DNA at 260 nm and transmitted to the dye, or irradiation absorbed at 300 nm and 360 nm by the bound dye itself, is emitted at 590 nm in the red-orange region of the visible spectrum. This dye can be used to detect both single- or double-stranded DNA. Strands of DNA larger than lkb are separated on agarose gels. Alkaline agarose gels are used to analyze the size of the DNA strand in DNA RNA hybrids that are nuclease-S1-resistant. They are also used to check the size of the first and second DNA stands synthesized by reverse transcriptase. DNA analyzed by alkaline gel electrophoresis is labeled with $^{32}P$, which can be detected with autoradiography. Polyacrylamide Gel electrophoresis is used to analyze and prepare fragments of DNA less than 1 kb in length. These gels are poured between two glass plates that are held apart by spacers to shield the acrylamide solution from exposure to air. This allows for the inhibition of polymerization by the oxygen to be restricted only to a narrow area at the top of the gel. The DNA embedded in polyacrylamide gels can be stained with ethidium bromide where the gel is submerged in staining solution containing ethidium bromide and thus can then be viewed and photographed under UV light. It can also be viewed using autoradiography where resulting bands are viewed and photographed under white light illumination. Strand separation of small DNA fragments, less than 200 nucleotide long, are separated using $^{32}P$ labeled DNA fragments and visualized using radiography techniques.

Gel Electrophoresis of RNA

There are two systems frequently used to measure the molecular weight of RNA and to separate RNA's of different sizes for different uses such as Northern blots or in-vitro translation. The first is agarose gel electrophoresis after denaturation of the RNA with glyoxal and dimethylsulfoxide. The second way is electrophoresis of agarose gels that contain methylmercuric hydroxide or formaldehyde. In each case, the RNA is fully denatured, and its rate of migration through the gel is in linear proportion to the $\log_{10}$ of its molecular weight. Ethidium bromide is used to detect single- and double-stranded RNA.

Methylene Blue

Methylene blue is another method to stain and visualize both DNA and RNA in gels. Separated bands appear blue in color when exposed to white light. It is used to stain DNA and RNA on agarose gels electrophoresis and for DNA fingerprinting visualization.

Autoradiography

Radioactive nucleic acids can be detected by autoradiography, for example for DNA sequence determination, Southern, Western, and Northern blots. Autoradiography is a sensitive method which gives a higher resolution, and does not involve destruction of the sample. The isotope $^{32}P$ is mostly used but other weaker β-emitting isotopes are also used for these purposes. The radioactively labeled nucleic acids are exposed for a period of several hours to several days onto X-ray film. The x-ray negatives developed are then visualized and/or photographed to analyzed and sequence determine the resulting nucleic acid band patterns under a uniform source of white light. In the cases of blots, Electrophoresis and staining of Proteins Fractionation of proteins in polyacrylamide gels is one of the primary means of their characterization due to its speed and ease of use. Many methods to separate both native (undenatured) and denatured proteins exists in the scientific literature. The most widely used technique, however, remains to be SDS polyacrylamide denaturing gel electrophoresis (SDS-PAGE). The goal of SDS-PAGE is to separate proteins based on molecular weight. SDS coats the proteins with negative charges so that during electrophoresis, the protein species will migrate towards to the cation side. The speed of migration depends upon the size of the protein. Lighter species will migrate faster thus will be further along on the gel than higher molecular weight proteins. The primary uses of SDS-PAGE are the determination of the size of a protein component, the estimation of protein purity in a solution, the purification of a protein species of other procedures, and the fractionation of a complex protein mixture prior to immunoblotting (Western blots). Two formats of gels are often used, mini-gels and large gels. Mini-gels are used generally for analytical and some preparative fractionation techniques, whereas the latter is used mainly for analytical separation and isolation of large amounts of denatured proteins. Detection of protein species in gels (visible bands) is usually performed post-electrophoretically using a number of dyes and are visualized and photographed under white light. However band resolution is better with less complex protein samples. Coomassie blue is the most general method used for quantifying 1- and 2-D gels with a densitometer. The staining process can take from 3 to 18 hours and can detect 40–50 ng of protein per band. This method is also used to determine if sufficient peptide is present on a membrane for sequencing. Fast Coomassie Stain is compatible with all Coomassie blue applications. It is a quick alternative to Coomassie blue method but band intensities are slightly less than with standard Coomassie stains. However, it provides a clear background. It is performed in 90 minutes and can detect 50 ng of proteins. Ghostband stains allow for fast and reversible negative staining of proteins, however these stains are not generally recommended for protein recovery. It a 15 minute method that can detect as little as 10–25 ng of protein per band. Silver stains are more sensitive than Coomassie blue detecting as little as 1–5 ng of protein per band. It is however, not recommended for quantification due to protein-to-protein variation and non-linearity of response. Other methods are used to detect the fractionate protein species besides staining. Many of these techniques rely on the transfer of SDS-PAGE-separated proteins to a membrane, others can be detected from the gel. Some of these techniques involve labeling proteins with $^{35}S$, $^{3}H$, $^{14}C$, and $^{125}I$. In such cases, the results are capture on X-ray film and one is able to use autoradiography to visualize the fractionated protein species. One method is using immunoblotting techniques including Western blots and dot blots, in which the sample to be examined is immobilized on a membrane prior to detection. Another common immunoblotting technique is colony/plaque lifts which uses similar procedures for detection. Colony/plaque lifts are used for cDNA expression libraries for clone identification. Western and dot blots are used in screening protein expression, including developmental changes, tissue-to-tissue differences, and in vitro translation reactions. They are also used in monitoring purification of proteins and screening monoclonals. Determining epitopes, however, is only performed using Westerns. Western blots, dot blots, and colony/plaque lifts all require the transfer, or immobilization, of a sample onto a membrane. This is the step where all three methods differ. In western blots, proteins are transferred to a membrane after PAGE; for dot blots non-denatured antigen-containing samples are spotted directly onto a membrane using a pipette. In colony/plaque lifts, intact colonies or plaques are transferred to a membrane, then lysed to expose and bind the potential antigen. Detection of blots and lifts are done through calorimetric reaction, chemiluminescence, and autoradiography.

Prior U. S. Letters Patent which relate to the field of this present invention are as follows:

1. U.S. Pat. No. 3,525,864 by Leach describes a process of removing the luminescent material from the inner surface of the gas discharge tube and instead coating the surface above the tube. The present invention utilizes the tubes with coating in place and uses the fluorescent dyed polymer material to create the required visible light.

2. U.S. Pat. No. 4,059,767 by Macovski describes an apparatus for enhancing the contrast of a transparency. It does not use ultraviolet light and is for transparencies only.

3. U.S. Pat. No. 5,554,449 by Tonomura, Matsui, and Morisyhta describes a high luminance thin film device that exhibits x-ray diffraction patterns. This device is not applicable to visible light emission.

SUMMARY OF PRESENT INVENTION

The application of the fluorescent dyed polymer is a new use for an existing product. The material was originally used in decorative and other applications put never in a technical application. Applying these products to the Biotech application of the Electrophoresis process provides a practicle and technically proficient means of expanding the use of the ultraviolet transillruminator to a wider range of gels for a low cost while conserving valuable laboratory bench space. The application of fluorescent dyed polymers to the transilluminator expands the visualization range from Ethidium bromide and Syber green stains to include Coomassie blue, Methylene blue, Silver stains plus many other visible light stains.

The application of the fluorescent dyed polymers to the ultraviolet transilluminator provides an expanded use of the unit allowing the visualization of all stained gels including the ultraviolet bandwidth and the visible bandwidth. This converts a single purpose device into a multipurpose device for a very practicle cost and conserving critical lab space.

A primary object resides in the application of fluorescent dyed polymers to ultraviolet transilluminators converts the unit to an ultraviolet and visible light transilluminator without changing sides.

Another object resides in the application of the fluorescent dyed polymer which can convert any unit already in use.

Still a further object resides in the application of fluorescent dyed polymer which can be customized to the particular stain used.

Another object of the invention resides in the cost reduction of the fluorescent dyed polymer which is a fraction of the cost of alternative white light approach.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following descriptions, taken in connection with the accompanying drawings in which:

FIG. 5 is a diagram showing Curve 1 which indicates a typical excitation curve for a fluorescent red dyed polymer.

DESCRIPTION OF THE PREFERRED EMBODIMENTS

Figure 2:
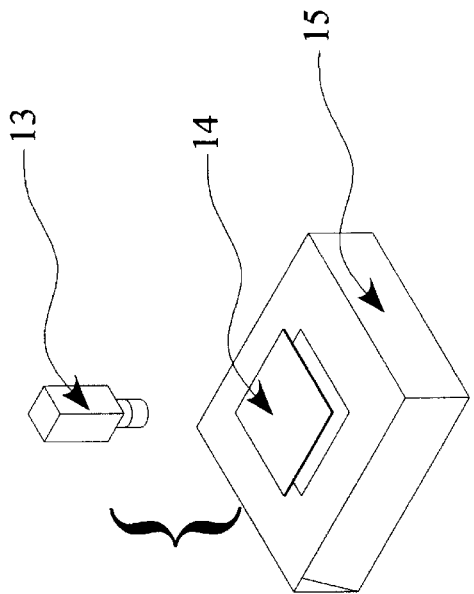
FIG. 2 is a drawing indicating the placement of the red dyed polymer sheet on an ultraviolet transilluminator and the position of a video camera.
Figure 4:
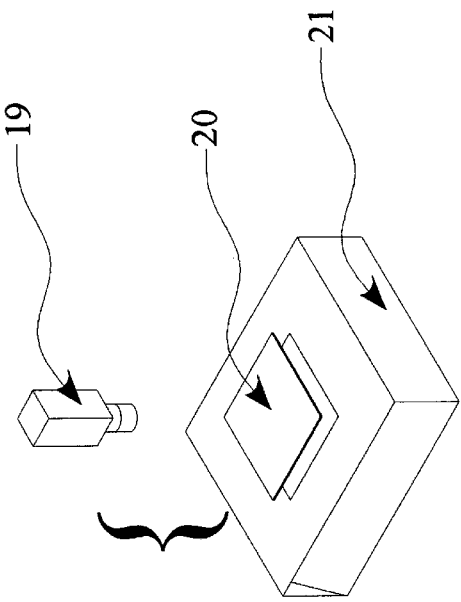
FIG. 4 is a drawing indicating the placement of the blue dyed polymer sheet on an ultraviolet transilluminator and the position of a video camera.
Figure 1:
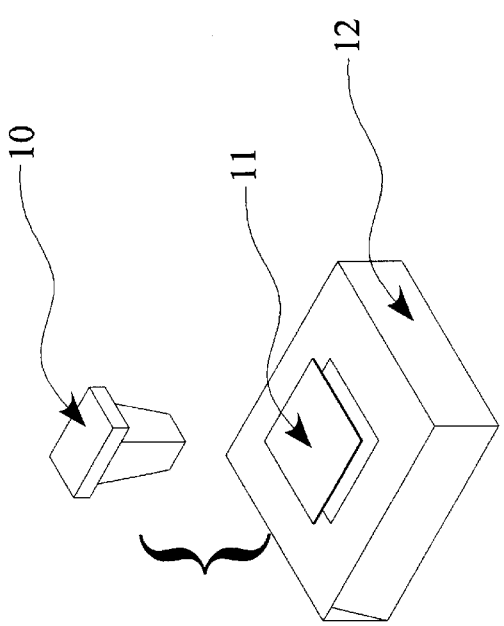
FIG. 1 is a drawing indicating the placement of the red dyed polymer sheet on an ultraviolet transilluminator and the position of a photographic camera.
Figure 3:
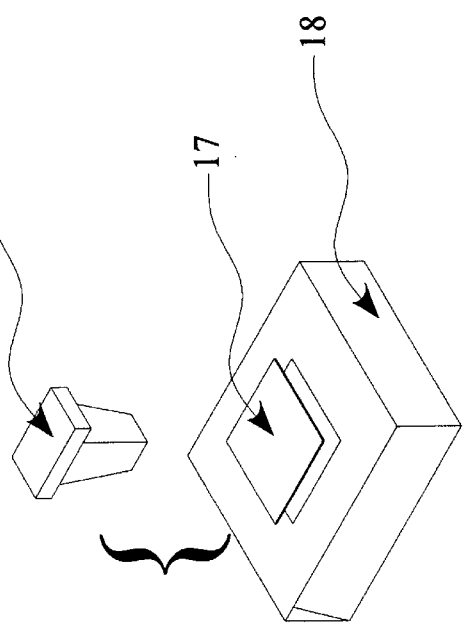
FIG. 3 is a drawing indicating the placement of the blue dyed polymer sheet on an ultraviolet transilluminator and the position of a photographic camera.
Figure 6:
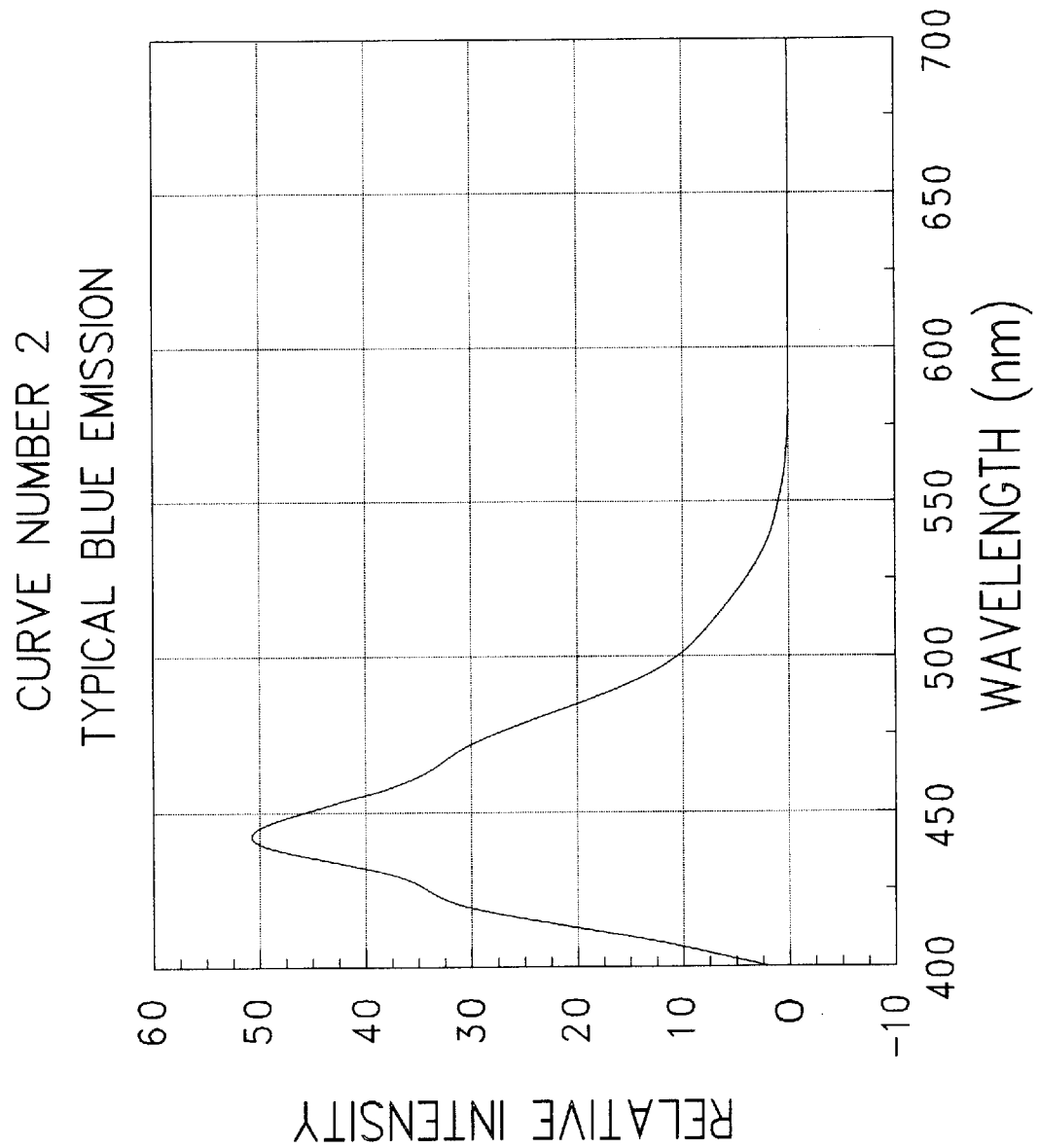
FIG. 6 is a diagram showing Curve 2 which indicates a typical excitation curve for a fluorescent blue dyed polymer.

The material is a fluorescent dyed polymer (e.g. acrylic) sheet which receives excitation energy from ultraviolet light and converts it to visible wavelength emissions. This conversion process allows one to use an ultraviolet light source, such as a ransilluminator as shown in FIG. 1, FIG. 2, FIG. 3 and FIG. 4 no. 10 and no. 16 are photographic cameras, no. 13 and no. 19 are video cameras, no. 12,15,18 and 21 represent ultraviolet transilluminators. no. 11 and 14 represent the placement of the red dyed polymer and no. 17 and 20 represent the placement of the blue dyed polymer to produce visible light for visualizing and documenting electrophoresis gels produced with visible stains (e.g. coomasie blue, silver stain). This material can be produced by various methods, for example cell casting, or extrusion. The actual base material may be any transparent polymer such as acrylic, polycarbonate, styrene or any appropriate copolymer. The dye stuffs for the polymer are chosen to provide the required fluorescence characteristics in terms of excitation and emission and for compatibility with the base polymer material. These materials are available commercially from a number of manufacturers under various brand names. Some examples are: Acrylite GPFL, Acrycast-MX, Plexiglas-FL.

They are supplied in sheet form with thickness from approximately 1/8" to several inches. The sheet dimensions can be supplied commonly up to 48"×96". The following curves show the excitation and emission for various colors of these materials. Several of these are quite useful for the imaging of electrophoresis gels. To produce high quality images the light source must be intense enough for the imaging device and the spectral characteristics must be compatible with the subject and the imaging device. Most imaging devices will work well with any visible source. The most common images used in electrophoresis processes are black and white film cameras and monochrome video cameras. Since both of these images respond to any visible light any color light may be used to illuminate the subject. The compatibility of the light source to the subject has to deal with the contrast of the image. If a subject is illuminated with light of the same color as its own color, the contrast is reduced. If the colors are complementary, the contrast is increased. Therefore, one would use a red light to view a blue subject and vice versa. Red dyed polymer excites well throughout the blue and ultraviolet band and emits in the orange-red region. Since this color complements coomasie blue stain it will produce high quality images when imaged with a suitably filtered black and white film camera or monochrome video camera. Blue dyed polymer also excites well with all ultraviolet wavelengths and is complementary to the reddish-brown tones of silver stain. These materials excitation and emission curves are shown in the accompanying graphs.

Therefore, it can be seen that the inventive concept converts ultraviolet light to visible light with fluorescent dyed polymer for photography and analysis of electrophoresis gels.

Visible light transillumination has been accomplished through the use of a white light transilluminator. This involved using two separate devices to visualize the fall family of gels. In recent years new devices were developed which contained two units built into one device. The unit was actually two separate transilluninators built into one cabinet. It required placing the gel on the ultraviolet side for ultraviolet actuated fluorescence or the white light side for visible light actuation. The cost over two units was slightly improved and space saving was somewhat improved. Very recently some white plastic has been introduced that has a special coating applied that is excited by 300 nanometer ultraviolet wavelength. Though this process has space saving characteristics, it also is more costly than the combined unit and has many technical restrictions.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An ultraviolet light to visible light converter means employing fluorescent dyed polymers comprising:
   an ultraviolet energy source;
   a sheet of material incorporating a fluorescent dyed polymer;
   a transilluminator for supporting said sheet of material incorporating said fluorescent dyed polymer and for housing said ultraviolet energy source; and
   a converter means carried on said sheet of material coactive with said fluorescent dyed polymer on said ultraviolet transilluminator for converting ultraviolet excitation energy from said ultraviolet energy source to visible light wavelengths.

2. The converter means defined in claim 1 wherein:
   said ultraviolet excitation energy is within the range of wavelengths from 200 nanometers to 370 nanometers.

3. The converter means defined in claim 2 wherein:
   said fluorescent dyed polymer is a red dye excited by nanometer wavelengths within said range of wavelengths which is combined with base stained gels produce visualization of subject undergoing analysis.

4. The converter means defined in claim 3 wherein:
   said base stained gels are chosen from:
   a. blue base stained gels;
   b. red base stained gels; and
   c. silver stained gels and other red base stains.

5. The converter means defined in claim 3 wherein:
   said base stained gels are electrophoresis gels.

6. The converter means defined in claim 1 wherein:
   said fluorescent dyed polymer is combined with a red dye excited by 365 nanometer wavelength to be used to visualize coomassie blue, methylene blue and other blue base stained gels.

7. The converter means defined in claim 1 wherein:
   said fluorescent dyed polymer is combined with a red dye excited by 300–312 nanometer wavelength to be used to visualize Coomassie blue, methylene blue and other blue base stained gels.

8. The converter means defined in claim 1 wherein:
   said fluorescent dyed polymer is combined with a red dye excited by 254 nanometer wavelength to be used to visualize Coomassie blue, methylene blue and other blue base stained gels.

9. The converter means defined in claim 1 wherein:
   said fluorescent dyed polymer is combined with a blue dye excited by 365 nanometer wavelength to be used to visualize silver stained gels and other red base stained gels.

10. The converter means defined in claim 1 wherein:
    said fluorescent dyed polymer is combined with a blue dye excited by 300–312 nanometer wavelength to be used to visualize silver stained gels and other red base stained gels.

11. The converter means defined in claim 1 wherein:
    said fluorescent dyed polymer is combined with a blue dye excited by 254 nanometer wavelength to be used to visualize silver stained gels and other red base stained gels.

12. An ultraviolet light to visible light converter means comprising:
    an ultraviolet energy source;
    a transilluminator housing said ultraviolet energy source and having a single window above said ultraviolet energy source;
    a sheet of material covering said window and incorporating fluorescent dyed polymer;
    a subject specimen residing on said sheet of material intended to be analyzed; and
    agarose gels applied to said subject specimen coacting with said fluorescent dyed polymer in response to excitation by said ultraviolet energy source to separate, identify and analyze said subject specimen.

13. The converter means defined in Claim 12 wherein:
    said ultraviolet energy source emits excitation energy within the range of wavelengths from 200 nanometers to 370 nanometers.

* * * * *